(12) United States Patent
Fujii et al.

(10) Patent No.: US 7,364,751 B2
(45) Date of Patent: Apr. 29, 2008

(54) STABILIZED COMPOSITIONS OF AQUEOUS REDUCED COENZYME Q SOLUTION

(75) Inventors: Kenji Fujii, Kobe (JP); Taizo Kawabe, Himeji (JP); Kazunori Hosoe, Takasago (JP); Takayoshi Hidaka, Kobe (JP)

(73) Assignee: Kaneka Corporation, Osaka (JP)

( * ) Notice: Subject to any disclaimer, the term of this patent is extended or adjusted under 35 U.S.C. 154(b) by 509 days.

(21) Appl. No.: 10/492,167

(22) PCT Filed: Oct. 10, 2002

(86) PCT No.: PCT/JP02/10516

§ 371 (c)(1),
(2), (4) Date: Jul. 21, 2004

(87) PCT Pub. No.: WO03/033445

PCT Pub. Date: Apr. 24, 2003

(65) Prior Publication Data

US 2005/0070481 A1  Mar. 31, 2005

(30) Foreign Application Priority Data

Oct. 10, 2001  (JP) ............................. 2001-312181

(51) Int. Cl.
*A61K 9/127* (2006.01)
*A61K 31/19* (2006.01)
*A61K 31/13* (2006.01)
*A61K 31/05* (2006.01)
*A01N 37/00* (2006.01)
*A01N 33/08* (2006.01)
*A01N 31/08* (2006.01)

(52) U.S. Cl. ...................... 424/450; 514/557; 514/667; 514/733; 514/718

(58) Field of Classification Search ..................... None
See application file for complete search history.

(56) References Cited

U.S. PATENT DOCUMENTS 6,066,327 A * 5/2000 Gubernick et al. ......... 424/401

6,420,437 B1  7/2002 Mori et al.
6,740,338 B1 * 5/2004 Chopra ...................... 424/456

FOREIGN PATENT DOCUMENTS

| EP | 882450 A2 | 12/1998 |
|---|---|---|
| EP | 1 415 969 A1 | 5/2004 |
| EP | 1 452 174 A1 | 9/2004 |
| JP | 54-119424 A | 9/1979 |
| JP | 5-186340 A | 7/1993 |
| JP | 7-69874 A | 3/1995 |
| JP | HEI-8-502300 | 3/1996 |
| JP | HEI-11-278843 | 10/1999 |
| JP | 2000-510841 A | 8/2000 |
| JP | 2001-019940 | 1/2001 |
| WO | WO 94/08624 | 4/1994 |
| WO | WO 97/42938 A1 | 11/1997 |
| WO | WO 98/07417 A1 | 2/1998 |
| WO | WO 00/61189 | 10/2000 |
| WO | WO 01/52822 A1 | 7/2001 |
| WO | WO 02/04025 A1 | 1/2002 |
| WO | WO 02/17879 A1 | 3/2002 |
| WO | WO 03/032967 A1 | 4/2003 |

OTHER PUBLICATIONS

Frei et al. Proc Natl Acad Sci USA 1990, 87, 4879-4883.*
PHARMACY, the First Edition, China Medical Technique Press, Apr. 2000, p. 103, line 18.
The application of Chelating Agent to Dyeing and Finishing Industry, Dyeing and Finishing, 2001, 27(1): 37-42.

* cited by examiner

*Primary Examiner*—John Pak
*Assistant Examiner*—Ernst Arnold
(74) *Attorney, Agent, or Firm*—Sughrue Mion, PLLC

(57) ABSTRACT

The present invention provides a reduced coenzyme Q-containing solution capable of being retained more stably against oxidation, by using a reduced coenzyme Q which is hydrophobic and susceptible to oxidation and thus unstable.

The aqueous solution containing a reduced coenzyme Q obtained in the present invention is a solution containing a reduced coenzyme Q and an antioxidant such as vitamin C and/or a chelating agent such as ethylenediaminetetraacetic acid.

3 Claims, No Drawings

STABILIZED COMPOSITIONS OF AQUEOUS REDUCED COENZYME Q SOLUTION

CROSS REFERENCE TO RELATED APPLICATION

This application is a 371 of PCT/JP02/10516 filed on Oct. 10, 2002 and claims foreign priority of Japanese Application No. 2001-312181 filed on Oct. 10, 2001.

TECHNICAL FIELD

The present invention relates to a solution containing a reduced coenzyme Q as a constituent and, more particularly, to an aqueous solution containing an antioxidant and/or a chelating agent added thereto for maintaining a reduced coenzyme Q stable against oxidation.

BACKGROUND ART

Coenzymes Q are essential constituents widely distributed in living bodies, from bacteria to mammals and are known as mitochondrial electron transfer system constituents in cells of living bodies. Through repeated oxidation and reduction in mitochondria, coenzymes Q perform their function as transmitter components in the electron transfer system and, further, reduced coenzymes Q are known to have antioxidant activity. In humans, coenzyme $Q_{10}$, whose coenzyme Q side chain comprises 10 repeating structures, is the main component and, generally, about 40 to 90% thereof occurs in reduced form in living bodies. The physiological activities of coenzymes Q may be energy production activation through mitochondrial activation, cardiac function activation, cell membrane stabilizing effect, and cell protecting effect through antioxidant activity.

Coenzymes Q are known to be useful in various application fields. For example, oxidized coenzyme $Q_{10}$ is used as a remedy for congestive heart failure owing to its effects on the heart. Besides such medical uses, they are orally used as nutrients or nutritional supplements, like vitamins. However, coenzymes Q are highly liposoluble and hardly soluble in water and, therefore, only oral preparations and dermal preparations are known as their practical uses.

In recent years, various reports have been published about the aggravation of diseases due to increases in oxidative stress in blood. Typical examples are arteriosclerosis, complications of diabetes and the like diseases. These diseases are caused and/or aggravated by denaturation of lipids and the like due to various oxidative stresses occurring in blood. For counteracting such effects of oxidative stresses, antioxidant activity promotion by administration of an antioxidant is effective. Vitamin E is a compound representative of the liposoluble antioxidant substances considered to be more effective in inhibiting lipid peroxidation and is in wide use in disease prevention and so on.

Recently, it has been reported that the coexistence of reduced coenzyme $Q_{10}$ is important for vitamin E to properly perform its antioxidant activity (Bowry et al., 1993, J. American Chemical Society, 115, 6029-6044), and the importance of coenzymes Q as liposoluble antioxidant substances is becoming clear.

Coenzymes Q have themselves strong antioxidant activity and, therefore, the antioxidant activity in blood can be effectively enhanced by sending a sufficient amount of reduced coenzymes Q in solubilized form into blood. The enhanced antioxidant activity in blood is considered to be useful widely in preventing vascular lesions during ischemia-reperfusion, preventing restenosis in arteriosclerosis, preventing vascular lesions following cerebral infarction, preventing arteriosclerosis, preventing complications of diabetes, and preventing a number of other diseases from being aggravated supposedly by active oxygen species. Furthermore, by sending it into the living body in a new delivery form, namely by drip, it becomes possible to provide patients with a serious illness or a brain disease, who are incapable of oral intake, with coenzymes Q. It is thus expected that solubilization of coenzymes Q will bring about a number of merits.

As is well known, coenzymes Q can occur in both the oxidized form and reduced form, and a number of investigations have so far been made about the method of solubilizing oxidized coenzyme $Q_{10}$ (ubidecarenone or ubiquinone).

As for the solubilization of oxidized coenzyme $Q_{10}$, various methods have been reported, for example coating with liposomes, suspension using a surfactant or an oil/fat, and the like (Japanese Kokai Publication Hei-05-186340, Japanese Kokai Publication Hei-07-69874, Japanese Kohyo Publication 2000-510841). However, few examples have been put to practice use. One of the reasons is that while it is necessary for oxidized coenzyme $Q_{10}$ to be converted to the reduced form by the action of a reductase or the like in order to perform its antioxidant activity, no reductase is present in blood and, therefore, no antioxidant activity against oxidative stresses in blood can be expected upon administration by injection or the like.

On the other hand, reduced coenzyme $Q_{10}$ itself has antioxidant activity, hence it is a substance much expected to be of great utility in the prevention/treatment of such diseases as mentioned above. However, it has not been put into practical use because of its drawback that it is susceptible to oxidation and thus unstable. Although a search report describing the preparation of liposome-coated reduced coenzyme $Q_{10}$ for the purpose of studying oxidoreductases and so forth is available (Kishi et al., 1999, BioFactors, 10, 131-138), the liposomes used were prepared extemporaneously in each experiment. Any method of stably solubilizing reduced coenzymes Q has not been known at all.

SUMMARY OF THE INVENTION

It is an object of the present invention to provide an aqueous solution improved in oxidation stability of reduced coenzymes Q.

The present inventors made investigations in an attempt to accomplish the above object and, as a result, found out an aqueous solution composition suitable for increasing the stability of reduced coenzymes Q, which has led to completion of the present invention.

Thus, the present invention provides an aqueous solution containing a reduced coenzyme Q, which comprises an antioxidant and/or a chelating agent in the same aqueous solution.

DETAILED DESCRIPTION OF THE INVENTION

The aqueous solution of the invention is an aqueous solution containing a reduced coenzyme Q represented by the following formula (1):

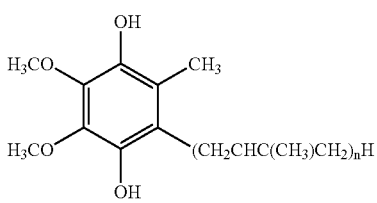

in the formula, n represents an integer of 1 to 12:
which comprises an antioxidant and/or a chelating agent in the same aqueous solution.

The coenzyme Q includes the species represented by the following formula (1):

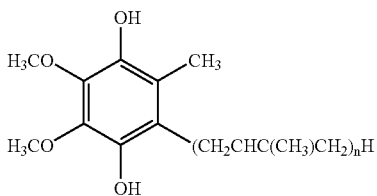

in the formula, n represents an integer of 1 to 12: and the species represented by the following formula (2):

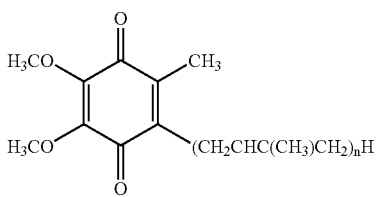

in the formula, n represents an integer of 1 to 12. The formula (1) represents the reduced form of a coenzyme Q and the formula (2) represents the oxidized form of a coenzyme Q.

In the practice of the invention, the coenzyme Q to be used may be any of those in which the number (n in the formulas) of repeating units in the side chain is 1 to 12, as represented by the above formulas (1) and (2). However, the one having 10 repeating units in the side chain, namely coenzyme $Q_{10}$, can be used most adequately.

In the practice of the invention, an oxidized coenzyme Q may coexist with the reduced coenzyme Q to be used. In that case, the content of the reduced coenzyme Q in the whole amount of coenzymes Q is preferably not less than 20% by weight, more preferably not less than 40% by weight, most preferably not less than 60% by weight.

The method of preparing the reduced coenzyme Q is not particularly restricted but, for example, the method comprising producing a coenzyme Q by any of the methods known in the art, for example by synthesis, fermentation, extraction from a natural source, or the like method and then concentrating the reduced coenzyme Q fraction in the eluate by chromatography can be employed. In this case, it is also possible to add a conventional reducing agent, such as sodium borohydride or sodium dithionite (hydrosulfite sodium), to the coenzyme Q if necessary and, after reduction of the oxidized coenzyme Q contained in the above coenzyme Q to a reduced coenzyme Q in the conventional manner, subject the reduction product to chromatography for concentration. It can also be obtained by the method comprising reacting a commercially available high-purity coenzyme Q with such a reducing agent as mentioned above.

The method of preparing the aqueous solution of the invention is not particularly restricted but, for example, the aqueous solution can be obtained (1) by coating a reduced coenzyme Q and an appropriate antioxidant and/or an appropriate chelating agent with an appropriate liposome base to give liposomes, (2) by adding an aqueous solution of an appropriate antioxidant and/or an appropriate chelating agent to reduced coenzyme Q-containing liposomes, or (3) by solubilizing or emulsifying a reduced coenzyme Q and an appropriate antioxidant and/or an appropriate chelating agent by means of an appropriate surfactant.

The aqueous solution of the invention is not particularly restricted but may be any one containing a reduced coenzyme Q and an antioxidant and/or a chelating agent. When it is prepared using liposomes, as mentioned above under (1) or (2), it occurs as an aqueous solution with the liposomes being dispersed in the aqueous solution. When it is prepared using a surfactant, as mentioned above under (3), it occurs as an aqueous solution with a reduced coenzyme Q being solubilized or emulsified therein.

The antioxidant that can be used in the practice of the present invention is not particularly restricted but includes, for example, citric acid, citric acid derivatives, vitamin C, vitamin C derivatives, probucol, lycopene, vitamin A, carotenoids, vitamin B, vitamin B derivatives, flavonoids, polyphenols, glutathione, selenium, sodium thiosulfate, vitamin E, vitamin E derivatives, superoxide dismutase (SOD), glutathione peroxidase, glutathione-S-transferase, glutathione reductase, catalase, ascorbate peroxidase and mixtures of these.

Among them, citric acid, citric acid derivatives, vitamin C, vitamin C derivatives, glutathione and sodium thiosulfate are preferred, vitamin C, citric acid and the like are more preferred, and vitamin C is still more preferred.

The chelating agent is not particularly restricted but includes, for example, ethylenediaminetetraacetic acid and salts thereof, ethylenediaminediacetic acid and salts thereof, hydroxyiminodiacetic acid and salts thereof, hydroxyethylethylenediaminetetraacetic acid and salts thereof, diethylenetriaminepentaacetic acid and salts thereof, nitrilotriacetic acid and salts thereof, triethylenetetraminehexaacetic acid and salts thereof, dicarboxymethylglutamic acid tetrasodium salt, dihydroxymethylglycine, 1,3-propanediaminetetraacetic acid and salts thereof, 1,3-diamino-2-hydroxypropanetetraacetic acid and salts thereof, sodium gluconate, hydroxyethylidenediphosphonic acid, alkylenephosphonic acids, phosphonobutanetricarboxylic acid and mixtures of these.

Among these, ethylenediaminetetraacetic acid and salts thereof, hydroxyethylethylenediaminetetraacetic acid and salts thereof, diethylenetriaminepentaacetic acid and salts thereof, sodium gluconate and hydroxyethylidenediphosphonic acid are preferred, and ethylenediaminetetraacetic acid and salts thereof are more preferred.

In cases where liposomes are used in the aqueous solution of the invention, the liposome includes, for example, phospholipids such as refined soy lecithin and phosphatidylcholine, glicolipids such as digalactosylglyceride, and the like. From the viewpoint of the stabilization of reduced coenzymes Q against oxidation, refined soy lecithin, phosphatidylcholine and the like are preferred.

When a surfactant is used in the aqueous solution of the invention, the surfactant is not particularly restricted but includes, for example, carboxylate salt type anionic surfactants and the like. Preferred from the viewpoint of the oxidation stability of reduced coenzymes Q are polysorbate 80, polyoxyethylene hydrogenated castor oil and the like.

The reduced coenzyme Q concentration in the aqueous solution of the invention is not particularly restricted but, from the viewpoint of oxidation stability, solubility in aqueous solution, and/or the like, the proportion of the reduced coenzyme weight to the volume of the aqueous solution is preferably not lower than 0.001% (w/v) but not higher than 5% (w/v), more preferably not lower than 0.05% (w/v) but not higher than 1% (w/v). The antioxidant concentration is not particularly restricted, either. From the efficacy viewpoint, however, it is preferably not lower than 0.01% (w/v) but not higher than 50% (w/v), more preferably not lower than 0.05% (w/v) but not higher than 10% (w/v), relative to the whole amount of the aqueous solution. The chelating agent concentration is not particularly restricted, either. From the efficacy viewpoint, however, it is preferably not lower than 0.001% (w/v) but not higher than 10% (w/v), more preferably not lower than 0.005% (w/v) but not higher than 5% (w/v), relative to the whole amount of the aqueous solution. The antioxidant concentration and chelating agent concentration mentioned above are applicable not only in the case where these are respectively used singly but also in the case of combined use thereof.

The pH of the aqueous solution of the invention is not particularly restricted but may vary according to the intended use thereof. From the viewpoint of the stability of coenzymes Q, however, the pH is preferably not lower than 1.0 but not higher than 8.0, more preferably not lower than 2.0 but not higher than 7.6.

To the aqueous solution to be prepared in the above manner, there may be added one or more other pharmaceutically acceptable preparation materials each at an appropriate addition level in the conventional manner. The preparation materials are not limited but there may be mentioned, for example, emulsifiers, isotonizing agents, buffers, solubilizing agents, correctives for smell, preservatives, stabilizers and the like. Furthermore, a further active ingredient, for example a drug and/or a nutritional supplement, may be added with the intended use.

The method of storing the aqueous solution composition according to the invention is not particularly restricted but includes cold storage (e.g. at −80° C. to 4° C.), anaerobic storage in a tightly closed container, and storage under protection from light, and the like.

The aqueous solution of the invention which can be prepared in the above manner can preserve reduced coenzymes Q more stably from oxidation.

The reduced coenzyme Q-containing aqueous solution according to the invention can be used in a wide range, including medical, cosmetic, food, horticultural, and dairy uses, and the like. As specific preparation forms, there may be mentioned injectable solutions, infusion solutions, liquid preparations, ophthalmic solutions, solutions for oral administration, lotions, hair tonics, milky lotions, sprays, aerosols, health drinks, liquid fertilizers, preserving solutions and so on. In the field of medicine, it can further be used as a preserving solution on the occasion of organ transplantation. Furthermore, the use as animal feeds and so on may also be mentioned. In addition, it can be used, as an antioxidant solution, in storing meat, fish and other perishable foods.

BEST MODE FOR CARRYING OUT THE INVENTION

The following examples illustrate the present invention in further detail. These examples are, however, by no means limitative of the scope of the invention.

EXAMPLE 1

Oxidation Stability of Liposome-Coated Reduced Coenzyme $Q_{10}$ as Given by an Antioxidant For evaluating the oxidation stability of reduced coenzyme $Q_{10}$ in liposomes, yolk lecithin (lecithin, product of Wako Pure Chemical Industries), which has poor oxidation stability, was selected as the liposome base, and the evaluation of substances capable of increasing the oxidation stability of reduced coenzyme $Q_{10}$ (content 0.005% w/v) was performed under the storage condition of 40° C.

Reduced coenzyme $Q_{10}$-containing liposomes were prepared by the following method. Thus, a powder of reduced coenzyme $Q_{10}$ was dissolved in ethanol to give a 0.1 mg/ml solution. Similarly, a lecithin solution (3.2 mg/ml) in ethanol was prepared. Both solutions (1 ml each) were mixed together. To the resulting mixture was added 2 ml of chloroform and, then, the solvent was removed under reduced pressure. After complete elimination of the solvents, 2 ml of a 50 mM HEPES buffer solution (pH 7.4) was added, and the lipid film was dispersed using a mixer to give a milk-white suspension. This suspension was subjected to sonication in a nitrogen atmosphere at 4° C. for 30 minutes for the formation of liposomes, followed by 20 minutes of centrifugation at 3,000 rpm to remove giant molecules as a sediment. The fraction remaining unsettled after centrifugation was used as reduced coenzyme $Q_{10}$-containing liposome solution.

Liposomes containing an antioxidant or a chelating agent (0.05% w/v) were prepared as follows. In the case of vitamin E, a 10 mg/ml ethanol solution was prepared and added to a mixed solution containing reduced coenzyme $Q_{10}$ and lecithin prior to the addition of chloroform in the above-mentioned process for preparing reduced coenzyme $Q_{10}$-containing liposomes and, thereafter, liposomes were prepared in the same manner as mentioned above. In the case of other water-soluble antioxidants or chelating agents, each antioxidant or chelating agent was dissolved in the above-mentioned HEPES buffer solution to a concentration of 0.05% (w/v) and, thereafter, liposomes were prepared in the same manner.

In this manner, liposomes containing various antioxidant (vitamin E acetate, sodium thiosulfate, citric acid, vitamin C, vitamin E (α-tocopherol)) were prepared and evaluated for oxidation stability during storage at 40° C. in the ambient atmosphere. The results were expressed in terms of residual reduced coenzyme $Q_{10}$ percentage.

For determining the residual reduced coenzyme $Q_{10}$ percentage, 1 ml of hexane was first added to 0.05 ml of each liposome solution and, after 30 seconds of stirring, the mixture was separated into a hexane layer and an aqueous layer by centrifugation (3,000 rpm, 1 minute). Then, the hexane layer was recovered and evaporated to dryness in a nitrogen atmosphere, the residue was dissolved in 0.2 ml of ethanol, and the solution was subjected to assaying by HPLC. The HPLC was carried out under per se known analytical conditions using an electrochemical detector, and oxidized coenzyme $Q_{10}$ and reduced coenzyme $Q_{10}$ were respectively quantitated. The residual reduced coenzyme $Q_{10}$ percentage was calculated as a percentage relative to the amount of reduced coenzyme $Q_{10}$ on the occasion of preparing liposomes.

As a result, the antioxidant-free liposomes underwent oxidation in such a manner that the residual percentage lowered to 10% or below during 1 to 2 days of storage, whereas the residual percentage was 63% after 2 days of storage in the case of vitamin E acetate-containing liposomes, 76% after 3 days of storage in the case of sodium thiosulfate-containing liposomes, 54% after 8 days of storage in the case of citric acid-containing liposomes, or 68% after 15 days of storage in the case of vitamin C-containing liposomes. However, the addition of vitamin E (α-tocopherol) failed to produce any remarkable effect.

It was thus found that some antioxidants are strongly effective and others are mildly effective in stabilizing reduced coenzyme $Q_{10}$ in liposomes. More specifically, vitamin C was the most effective, followed by citric acid, sodium thiosulfate, vitamin E acetate, and vitamin E in that order.

EXAMPLE 2

Oxidation Stability of Liposome-Coated Reduced Coenzyme $Q_{10}$ as Given by a Chelating Agent The effect of a chelating agent on the residual reduced coenzyme $Q_{10}$ percentage was evaluated in the same manner as in Example 1. Liposomes containing 0.05% (w/v) of ethylenediaminetetraacetic acid were prepared in the same manner as in Example 1 and stored in the air at 40° C. for evaluating the stabilizing effect of the chelating agent.

The reduced coenzyme $Q_{10}$ in chelating agent-free liposomes was oxidized to a residual percentage of 10% or below during 1 to 2 days of storage, whereas the ethylenediaminetetraacetic acid-containing liposomes showed a residual percentage of 76% after 43 days of storage.

It is known in the art that the chelating agent ethylenediaminetetraacetic acid is more or less effective in protecting substances susceptible to oxidation. However, the finding obtained in this example that it is comparable or superior in such protective effect to antioxidants was quite unexpected.

EXAMPLE 3

Effect of an Antioxidant on a Surfactant Solution—(1)

To a 0.1% aqueous polysorbate 80 solution containing 0.005% (w/v) of reduced coenzyme $Q_{10}$ was added vitamin C, as an antioxidant, to a concentration of 0.05% (w/v), the solution was stored at 40° C., and the effect of the antioxidant was evaluated.

The solution without addition of the antioxidant gave a residual percentage of 27% after 6 days of storage. On the contrary, 88% of the reduced form was retained in the vitamin C-containing solution even after 6 days of storage.

EXAMPLE 4

Effect of an Antioxidant on a Surfactant Solution—(2)

To a solution containing 0.1% of polyoxyethylene hydrogenated castor oil (HCO-60; product of Nikko Chemicals) and 0.005% (w/v) of reduced coenzyme $Q_{10}$ was added vitamin C or citric acid, as an antioxidant, to a concentration of 0.05% (w/v), the solution was stored at 40° C., and the effect of the antioxidant was evaluated.

The solution without addition of the antioxidant gave a residual percentage of 17% after 7 days of storage. On the contrary, 73% of the reduced form was retained in the vitamin C-containing solution even after 14 days of storage, and 61% of the reduced form was maintained in the citric acid-containing solution even after 71 days of storage.

EXAMPLE 5

Effect of a Chelating Agent on a Surfactant Solution—(1)

The effect of a chelating agent was evaluated in the same manner as in Example 3 except that ethylenediaminetetraacetic acid was used as the chelating agent in lieu of the antioxidant.

The solution without addition of the chelating agent gave a residual percentage of 27% after 6 days of storage, whereas 80% of the reduced form was retained in the ethylenediaminetetraacetic acid-containing solution even after 78 days of storage, indicating the same potent protective effect as in the case of liposomes.

EXAMPLE 6

Effect of a Chelating Agent on a Surfactant Solution—(2)

The effect of a chelating agent was evaluated in the same manner as in Example 4 except that ethylenediaminetetraacetic acid was used as the chelating agent in lieu of the antioxidant.

The solution without addition of the chelating agent gave a residual percentage of 17% after 7 days of storage, whereas 74% of the reduced form was retained in the ethylenediaminetetraacetic acid-containing solution even after 167 days of storage. The result obtained that reduced coenzyme $Q_{10}$ can be maintained at high residual percentages under such high temperature conditions as 40° C. over a period as long as nearly half a year was quite unexpected.

INDUSTRIAL APPLICABILITY

In accordance with the invention, liquid preparations containing reduced coenzymes Q, which are highly useful as antioxidant substances or nutritional supplement components, can be provided more stably.

The invention claim is:
1. An aqueous solution, comprising:
a reduced coenzyme Q represented by the following formula (1):

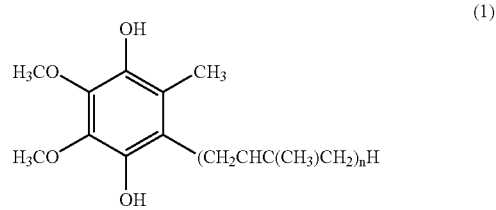

in the formula, n represents an integer of 1 to 12;
a liposome containing the reduced coenzyme Q; and ethylenediaminetetraacetic acid or a salt thereof in an amount effective to stabilize said reduced coenzyme Q.

2. The aqueous solution according to claim 1, wherein the liposome further contains ethylenediaminetetraacetic acid or a salt thereof.

3. The aqueous solution according to claim 1, wherein the reduced coenzyme Q is reduced coenzyme $Q_{10}$.

* * * * *